(12) United States Patent
Rai et al.

(10) Patent No.: US 8,367,354 B2
(45) Date of Patent: Feb. 5, 2013

(54) METHODS FOR DETERMINING THE LEVELS OF TGF-β IN A COMPOSITION

(75) Inventors: Gyan P. Rai, Newburgh, IN (US); Francisco J. Rosales, Newburgh, IN (US); Zeina E. Jouni, Evansville, IN (US); Rosaline Waworuntu, Evansville, IN (US)

(73) Assignee: Mead Johnson Nutrition Company, Evansville, IN (US)

( * ) Notice: Subject to any disclaimer, the term of this patent is extended or adjusted under 35 U.S.C. 154(b) by 824 days.

(21) Appl. No.: 12/370,469

(22) Filed: Feb. 12, 2009

(65) Prior Publication Data

US 2010/0105083 A1 Apr. 29, 2010

Related U.S. Application Data

(60) Provisional application No. 61/108,315, filed on Oct. 24, 2008.

(51) Int. Cl.
*G01N 33/00* (2006.01)

(52) U.S. Cl. ....... 435/7.92; 435/7.1; 435/7.94; 436/501; 436/518

(58) Field of Classification Search .......................... None
See application file for complete search history.

(56) References Cited

U.S. PATENT DOCUMENTS

| | | | |
|---|---|---|---|
| 5,290,571 A | 3/1994 | Bounous et al. |
| 5,451,412 A | 9/1995 | Bounous et al. |
| 5,461,033 A | 10/1995 | Donnet et al. |
| 5,866,418 A | 2/1999 | Ballard et al. |
| 5,952,295 A | 9/1999 | Arnaud-Battandier et al. |
| 6,177,550 B1 | 1/2001 | Meyer et al. |
| 6,194,208 B1 | 2/2001 | Belford et al. |
| 6,319,522 B1 | 11/2001 | Ballard et al. |
| 6,395,494 B1 | 5/2002 | Grainger et al. |
| 6,447,808 B2 | 9/2002 | Ballard et al. |
| 6,733,770 B1 | 5/2004 | Garcia-Rodenans et al. |
| 7,141,262 B2 | 11/2006 | Maubois et al. |
| 2003/0232057 A1 | 12/2003 | Turini et al. |
| 2004/0102377 A1 | 5/2004 | Perrin et al. |
| 2004/0219225 A1 | 11/2004 | Kivits et al. |
| 2005/0250697 A1 | 11/2005 | Maubois et al. |
| 2006/0293228 A1 | 12/2006 | Bhatnagar |

FOREIGN PATENT DOCUMENTS

| | | |
|---|---|---|
| EP | 0313515 | 3/1992 |
| EP | 0339656 | 11/1994 |
| EP | 0374390 | 6/1995 |
| EP | 0527283 | 11/1997 |
| EP | 0852913 | 7/1998 |
| EP | 0759029 | 7/1999 |
| EP | 1034704 | 9/2000 |
| EP | 1161152 | 10/2004 |
| EP | 0545946 | 1/2005 |
| EP | 1218410 | 6/2005 |
| EP | 1345624 | 6/2006 |
| EP | 1779863 | 5/2007 |
| WO | 9200994 | 1/1992 |
| WO | 9818816 | 5/1998 |
| WO | 0054603 | 9/2000 |
| WO | 0125276 | 4/2001 |
| WO | 02051437 | 7/2002 |
| WO | 02083164 | 10/2002 |
| WO | 2005039318 | 5/2005 |

OTHER PUBLICATIONS

Oddy et al., TGF-B in human milk is associated with wheeze in infancy, J. Allergy. clin. Immunol. vol. 112, No. 4, Oct. 2003, pp. 723-728.*
Quantikine Human TGF-B1 Immunoassay, May 2008.
Quantikine Human TGF-B2 Immunoassay, Jun. 2008.
Saito, et al., Transforming Growth Factor-Beta (TGF-B) in Human Milk, Clinical and Experimental Immunology, Oct. 1993, vol. 94, No. 1, pp. 220-224.

* cited by examiner

*Primary Examiner* — Gary W Counts
(74) *Attorney, Agent, or Firm* — Waddey & Patterson, P.C.; James R. Cartiglia; Rebecca M. Barnett

(57) ABSTRACT

A novel method for determining the levels of TGF-β1 or TGF-β2 in a sample of milk, raw protein source, or nutritional composition is provided. The method involves, in some cases, reconstituting the sample; in some cases, centrifuging the sample; activating the sample using particular ratios of sample:acid:base; diluting the sample using particular ratios of sample:buffer agent; and determining the concentration of TGF-β1 in the sample using an ELISA assay.

5 Claims, 1 Drawing Sheet

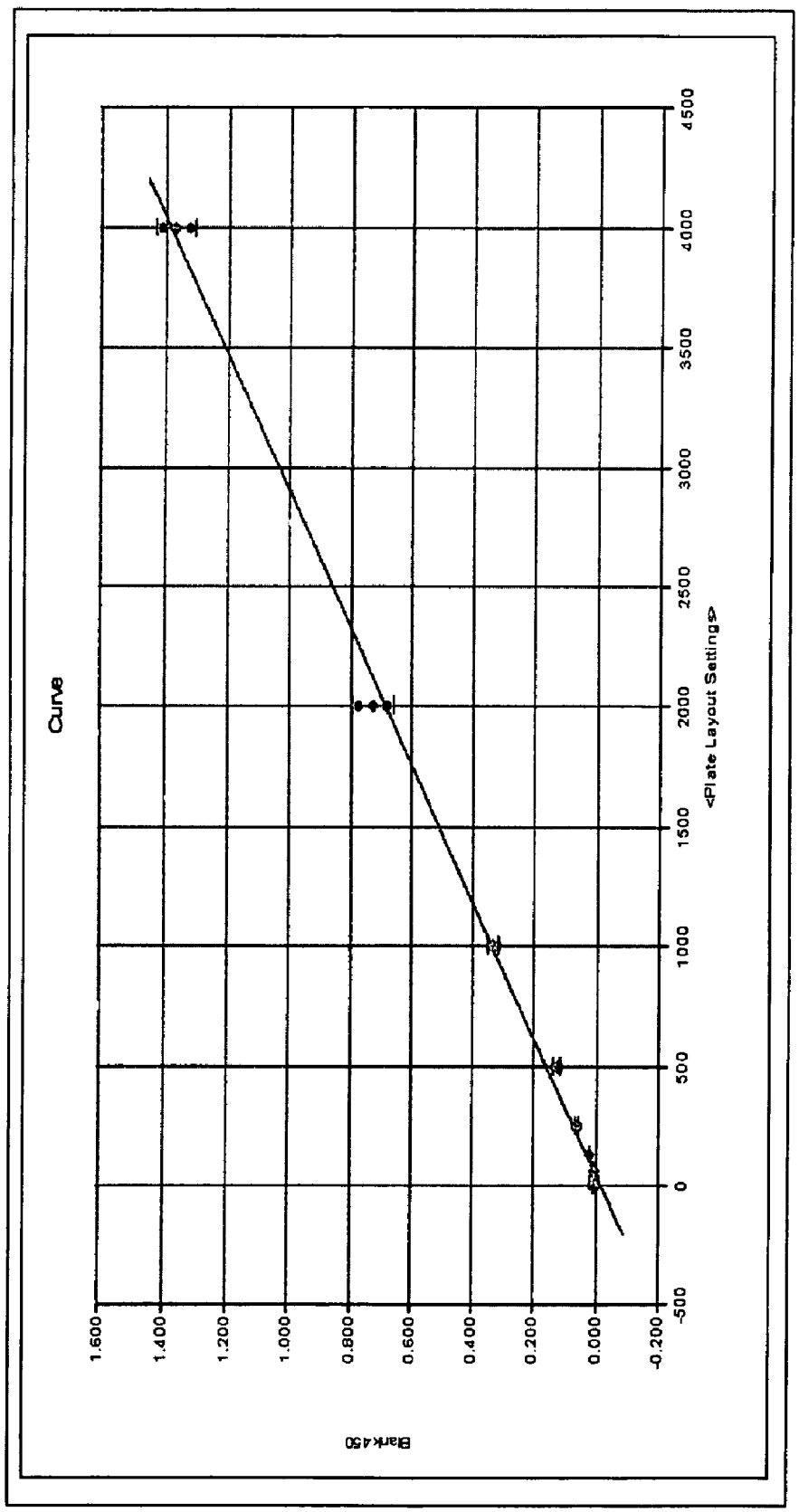

METHODS FOR DETERMINING THE LEVELS OF TGF-β IN A COMPOSITION

CROSS-REFERENCES TO RELATED APPLICATIONS

This application claims benefit of the following patent application(s) which is/are hereby incorporated by reference: U.S. Provisional Application Ser. No. 61/108,315 filed Oct. 24, 2008.

BACKGROUND OF THE INVENTION (1) Field of the Invention

The present invention relates generally to methods of determining the level of transforming growth factor-β (TGF-β) in a composition.

SUMMARY OF THE INVENTION

In an embodiment, the present invention is directed to a method for determining the level of TGF-β1 in a sample of milk, the method comprising:
  a. centrifuging the sample for about 15 minutes at a centrifugal force of about 10,000 rpm;
  b. collecting the aqueous phase supernatant of the sample and repeating step (a) using the supernatant of step (a);
  c. collecting the aqueous phase supernatant of the sample from step (b) and repeating step (a) using the supernatant of step (b);
  d. activating the sample by adding an acid and a base in a ratio of sample:acid:base of about 1:0.2:0.2;
  e. diluting the sample using a buffer solution at a ratio of at least about 1:2 (sample:buffer); and
  f. determining the concentration of TGF-β1 in the sample comprising the steps:
    i. immobilizing the sample having an unknown amount of TGF-β1 on a solid support;
    ii. adding at least one detection antibody to form a complex with the TGF-β1;
    iii. adding at least one enzymatic substrate to produce a visible signal; and
    iv. detecting the visible signal to determine the amount of TGF-β1 in the sample.

In an embodiment, the present invention is directed to a method for determining the level of TGF-β2 in a sample of milk, the method comprising:
  a. centrifuging the sample for about 15 minutes at a centrifugal force of about 10,000 rpm;
  b. collecting the aqueous phase supernatant of the sample and repeating step (a) using the supernatant of step (a);
  c. collecting the aqueous phase supernatant of the sample from step (b) and repeating step (a) using the supernatant of step (b);
  d. activating the sample by adding an acid and a base in a ratio of sample:acid:base of about 1:0.2:0.2; and
  e. determining the concentration of TGF-β2 in the sample comprising the steps:
    i. immobilizing the sample having an unknown amount of TGF-β2 on a solid support;
    ii. adding at least one detection antibody to form a complex with the TGF-β2;
    iii. adding at least one enzymatic substrate: to produce a visible signal; and
    iv. detecting the visible signal to determine the amount of TGF-β2 in the sample.

In an embodiment, the present invention is directed to a method for determining the level of TGF-β1 in a sample of powdered nutritional product, the method comprising:
  a. reconstituting the nutritional product to a concentration of from about 160 mg/mL to about 170 mg/mL;
  b. avoiding a centrifuging step;
  c. activating the sample by adding an acid and a base in a ratio of sample:acid:base of about 1:0.2:0.2;
  d. diluting the sample using a buffer solution at a ratio of at least about 1:4 (sample:buffer);
  e. determining the concentration of TGF-β1 in the sample comprising the steps:
    i. immobilizing the sample having an unknown amount of TGF-β1 on a solid support;
    ii. adding at least one detection antibody to form a complex with the TGF-β1;
    iii. adding at least one enzymatic substrate to produce a visible signal; and
    iv. detecting the visible signal to determine the amount of TGF-β1 in the sample.

In an embodiment, the present invention is directed to a method for determining the level of TGF-β2 in a sample of powdered nutritional product, the method comprising:
  a. reconstituting the nutritional product to a concentration of from about 160 mg/mL to about 170 mg/mL;
  b. avoiding a centrifuging step;
  c. activating the sample by adding an acid and a base in a ratio of sample:acid:base of about 1:0.2:0.2;
  d. diluting the sample using a buffer solution at a ratio of at least about 1:8 (sample:buffer);
  e. determining the concentration of TGF-β2 in the sample comprising the steps:
    i. immobilizing the sample having an unknown amount of TGF-β2 on a solid support;
    ii. adding at least one detection antibody to form a complex with the TGF-β2;
    iii. adding at least one enzymatic substrate to produce a visible signal; and
    iv. detecting the visible signal to determine the amount of TGF-β2 in the sample.

In an embodiment, the present invention is directed to a method for determining the level of TGF-β1 in a sample of powdered raw protein source, the method comprising:
  a. reconstituting the raw protein source to a concentration of from about 95 mg/mL to about 105 mg/mL;
  b. avoiding a centrifuging step;
  c. activating the sample by adding an acid and a base in a ratio of sample:acid:base of about 1:0.2:0.225;
  d. diluting the sample using a buffer solution at a ratio of at least about 1:2 (sample:buffer);
  e. determining the concentration of TGF-β1 in the sample comprising the steps:
    i. immobilizing the sample having an unknown amount of TGF-β1 on a solid support;
    ii. adding at least one detection antibody to form a complex with the TGF-β1;
    iii. adding at least one enzymatic substrate to produce a visible signal; and
    iv. detecting the visible signal to determine the amount of TGF-β1 in the sample.

In an embodiment, the present invention is directed to a method for determining the level of TGF-β2 in a sample of powdered raw protein source, the method comprising:
  a. reconstituting the raw protein source to a concentration of from about 95 mg/mL to about 105 mg/mL;
  b. avoiding a centrifuging step;

c. activating the sample by adding an acid and a base in a ratio of sample:acid:base of about 1:0.2:0.2;

d. diluting the sample using a buffer solution at a ratio of at least about 1:9 sample:buffer; and e. determining the concentration of TGF-β2 in the sample comprising the steps:

i. immobilizing the sample having an unknown amount of TGF-β2 on a solid support;

ii. adding at least one detection antibody to form a complex with the TGF-β2;

iii. adding at least one enzymatic substrate to produce a visible signal; and iv. detecting the visible signal to determine the amount of TGF-β2 in the sample.

In yet another embodiment, the invention is directed to a kit for measuring TGF-β in milk, nutritional products, or raw protein sources, the kit comprising: a TGF-β conjugate; a TGF-β standard; a diluent; a wash buffer; at least one color reagent; and a stop solution.

BRIEF DESCRIPTION OF THE DRAWINGS

FIG. 1 illustrates the standard curve, as described in the specification at Table 3.

DETAILED DESCRIPTION OF THE PREFERRED EMBODIMENTS

Reference now will be made in detail to the embodiments of the invention, one or more examples of which are set forth below. Each example is provided by way of explanation of the invention, not a limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment.

Thus, it is intended that the present invention covers such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

As set forth above, the present invention relates generally to methods for determining the levels of TGF-β in various samples. References related to such methods may include U.S. Pat. No. 6,194,208.

Transforming growth factor-beta (TGF-β) is the general name for a family of polypeptides, the members of which have multifunctional regulatory activities. Three differentially regulated mammalian isoforms (termed TGF-β1, TGF-β2, and TGF-β3) play important roles in a multitude of processes in the developing embryo, infant, child and adult. TGF-β is a 25-kDa homodimeric cytokine known to mediate pleitropic functions both within the immune system and systemically. TGF-β is expressed in several cell types in the intestinal mucosal including lymphocytes, epithelial cells, macrophages, and stromal cells as well as by T-cells, neutrophils, macrophages, epithelial cells, fibroblasts, platelets, osteoblasts, osteoclasts and others. In addition, TGF-β is present in human breast milk and may influence multiple aspects of infant health and development.

TGF-βs are synthesized as large precursor proteins which consist of an amino-terminal pro-domain, comprising a signal sequence and latency-associated complex, and a mature carboxy-terminal subunit. Biologically active TGF-βs are homodimers which consist of two identical, disulfide-linked mature subunits. Release of the TGF-β homodimer from the latency-associated complex is necessary for TGF-β to exert biological activity on target cells. The nature of the latency-associated complex and the mechanisms responsible for TGF-β release are key to understanding TGF-β biological activity in vivo. In the human gut, this may be accomplished by the action of proteolytic enzymes, pH extremes, heat, calcium, and/or mechanical tearing.

Based on the numerous benefits provided by TGF-β, it is often important that the growth factor is present in, or supplemented into, various nutritional products. For example, certain protein sources in nutritional products may provide a source of TGF-β. Alternatively, if the nutritional product itself does not contain TGF-β, the growth factor may be supplemented into the product. As noted above, however, the release of TGF-β is in its inactive form. The TGF-β present in the protein sources of nutritional products, or added to those nutritional products, is also in its inactive form. It is then activated in the human gut by enzymes, extremes of pH, and/or tearing.

Based on the numerous benefits provided by TGF-β, it is often important that the growth factor is present in, or supplemented into, various liquid nutritional products. Until the present invention, however, there has not been an effective method for determining the levels of TGF-β in a sample of milk, nutritional product, or raw protein source, such as whey protein concentrate. In part, this may be due to high variability within and between studies reporting concentrations of TGF-β in these compositions. Moreover, there is relatively little knowledge of the factors affecting these reported levels in milk, nutritional products, or raw protein sources.

Thus, the technical problem to be solved by the present invention is to provide an accurate and reproducible method for determining TGF-β levels, including both TGF-β1 and TGF-β2, in a composition. In accordance with the present invention, the inventors have discovered a novel method for determining the levels of TGF-β in a sample of milk, nutritional product, or raw protein source.

As set forth above, the method of the invention may be used to determine the levels of TGF-β in milk sources. In this embodiment, the milk may be human milk, bovine milk, goat milk, sheep milk, or any other milk sourced from a mammal.

In another embodiment, the method of the invention may be used to determine the levels of TGF-β in a nutritional product. The nutritional product may be an infant formula. In some embodiments, the nutritional product may be an infant formula. The term "infant formula" applies to a composition in liquid or powdered form intended for use, where necessary, as a substitute for human milk (breast milk substitute) in meeting the normal nutritional requirements of infants. In a separate embodiment, the nutritional product may be a human milk fortifier, meaning it is a composition which is added to human milk in order to enhance the nutritional value of human milk. As a human milk fortifier, the inventive composition may be in powder or liquid form. In another embodiment, the inventive nutritional product may be a follow-up formula. The term "follow-up formula" as used herein refers to foods intended for use as a liquid part of the weaning diet for the infant from the $6^{th}$ month of life on and for young children. In yet another embodiment, the inventive nutritional product may be a children's nutritional composition. The term "child" or "children" as used herein means persons over the age of 3 years and prior to adolescence. In still another embodiment, the inventive nutritional product may be a growing-up milk. The term "growing-up milk" refers to a broad category of milk-based fortified beverages intended to be used as a part of a diverse diet in order to support the normal growth and development of children from the ages of 1 to 6 years.

In some embodiments, the composition is an acidified product. As used herein, the term "acidified product" refers to a nutritional composition which has a finished equilibrium pH of 4.6 or below and a water activity greater than 0.85. In still another embodiment, the nutritional product may be a medical food. The term "medical food" is defined as a food which is formulated to be consumed or administered enterally under the supervision of a physician and which is intended for the specific dietary management of a disease or condition for which distinctive nutritional requirements, based on recognized scientific principles, are established by medical evaluation. In general, to be considered a medical food, a product must, at a minimum, meet the following criteria: the product must be a food for oral or tube feeding; the product must be labeled for the dietary management of a specific medical disorder, disease or condition for which there are distinctive nutritional requirements; and the product must be intended to be used under medical supervision.

In yet another embodiment, the method of the invention may be used to determine the levels of TGF-$\beta$ in a raw protein source, such as whey protein concentrate, non-fat dry milk, or casein protein.

The composition of the invention may be provided in any form known in the art, such as a powder, a gel, a suspension, a paste, a solid, a liquid, a liquid concentrate, or a ready-to-use product.

Enzyme linked immunosorbent assay ("ELISA") kits are often used to measure TGF-$\beta$1 or TGF-$\beta$2 levels in cell culture supernates, serum, plasma, and/or urine. The ELISA kits from R&D Systems, Quantikine 1 (Cat. No. DB100B) for TGF-$\beta$1 and Quantikine 2 (Cat. No. DB250) for TGF-$\beta$2, are often used for these purposes. Currently, however, there are no commercially available ELISA kits for accurately measuring TGF-$\beta$1 or TGF-$\beta$2 in milk, nutritional products, or raw protein sources.

Generally speaking, ELISA is a rapid immunochemical test that involves an enzyme (a protein that catalyzes a biochemical reaction) and an antibody or antigen (immunologic molecules). In the present invention, the antibody that is used will be specific for TGF-$\beta$ (the antigen). The ELISA method involves using an antibody which is attached to a solid surface. This antibody has affinity for (will latch onto) the substance of interest, for example, TGF-$\beta$ present in a composition. A mixture of purified TGF-$\beta$ linked (coupled) to an enzyme and the test sample are added to the test system. Between each step, the plate is typically washed with a mild detergent solution to remove any proteins or antibodies that are not specifically bound. If no TGF-$\beta$ is present in the test sample, then only TGF-$\beta$ with linked enzyme will bind. The more TGF-$\beta$ which is present in the test sample, the less enzyme-linked TGF-$\beta$ will bind. The substance the enzyme acts on is then added, and the amount of product measured in some way, such as a change in color of the solution.

ELISA tests are generally highly sensitive and specific and compare favorably with radioimmune assay tests. They have the added advantages of not needing radioisotopes or a radiation-counting apparatus.

In some embodiments of the present invention, the ELISA assay may employ the quantitative sandwich enzyme immunoassay technique, understood by one of skill in the art.

Generally speaking, a monoclonal antibody specific for TGF-$\beta$1 or TGF-$\beta$2 may be pre-coated onto a microplate. In the present invention, this monoclonal antibody may be a purified mouse monoclonal anti-TGF-$\beta$. Any remaining binding sites may be blocked. Standards, controls, and samples may then be pipetted into the wells of the microplate. In some embodiments of the invention, the standard utilized is a porcine TGF-$\beta$ standard or a recombinant human TGF-$\beta$ standard.

The standard, control, and samples are then incubated with a biotin-labeled detection antibody, which binds to a different epitope of TGF-$\beta$, completing the sandwich. In an embodiment, the detection antibody may be biotinylated affinity purified goat IgG.

Between each step, the plate is washed with a mild detergent solution to remove any proteins or antibodies that are not specifically bound. The amount of detection antibody bound to TGF-$\beta$ is then detected by a detection reagent following incubation with an appropriate enzymatic substrate. In an embodiment, the detection reagent may be streptavidin-Horseradish Peroxidase. A visible signal which correlates with the quantity of TGF-$\beta$ in the samples is measured with a microplate reader. The greater the signal, the greater the concentration of TGF-$\beta$ throughout the range of the standard curve.

An embodiment of the ELISA testing of the present invention is set forth in the flow chart below.

ELISA FLOW CHART:

Coat the plate 100 µl/well with 2 µg/ml Purified Mouse
Monoclonal Anti-TGF-$\beta$2
(For 1 plate: 40 µl mAb in 9960 µl CBC buffer)
Incubate O/N at 4° C.

↓

Wash plate 3 times

↓

Block the plate with SEA Blocking Buffer, 270 µl /well
Incubate at RT for 1 hour

↓

Wash plate 3 times

↓

Add 100 µl/well standard and sample, diluted with PBS
Incubate at RT for 1.5 hours with shaking (±500 rpm)

↓

Wash plate 3 times

↓

Add 100 µl/well; 75 ng/ml Anti-TGF-$\beta$2 Biotinylated pAb
(For 1 plate: 15 µl in 10 ml PBS
Incubate at RT for 2 hours with shaking

↓

-continued

Wash plate 3 times

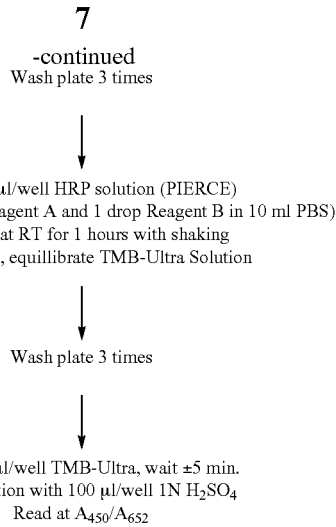

Add 100 µl/well HRP solution (PIERCE)
(For 1 plate: 1 drop Reagent A and 1 drop Reagent B in 10 ml PBS)
Incubate at RT for 1 hours with shaking
At this time, equillibrate TMB-Ultra Solution Wash plate 3 times Add 100 µl/well TMB-Ultra, wait ±5 min.
Stop reaction with 100 µl/well 1N $H_2SO_4$
Read at $A_{450}/A_{652}$ The sandwich method need not be the only ELISA method utilized in this invention. Any ELISA assay technique may be used, as modified herein, in the method of the invention.

Prior to the ELISA assay, powdered samples may be reconstituted. For example, a powdered nutritional supplement such as infant formula, or a raw protein source such as whey protein concentrate, may be reconstituted to a liquid form. It was discovered in the present invention that samples comprising a raw protein source, such as whey protein concentrate, may be reconstituted differently than nutritional products, such as infant formula. Thus, in the present invention, a nutritional product, such as infant formula, may be reconstituted to a concentration of from about 160 mg/mL to about 170 mg/mL. In another embodiment, the nutritional product may be reconstituted to about 166 mg/mL. In a particular embodiment, the reconstitution of the nutritional product comprises dissolving about 0.5 g powdered nutritional product in about 3 mL water.

With regard to raw protein sources, however, such as whey protein concentrate or non-fat dry milk, the sample may be reconstituted to a concentration of from about 95 mg/mL to about 105 mg/mL. In a particular embodiment, the sample may be reconstituted to about 100 mg/mL. This may be achieved via dissolution of about 0.5 g powder in about 5 mL water. This reconstitution concentration is required for the raw protein source in order for the sample to move from a suspension to a solution.

In preparing a sample for ELISA testing, the sample is typically centrifuged in order to defatten the sample and collect the aqueous phase supernatant (i.e. whey fraction) for testing. In the present invention, the inventors have discovered that human milk may be centrifuged approximately 3 times for about 15 minutes each at 10,000 rpm. This method effectively removes the lipid layer from the milk. However, for nutritional products such as infant formula, or raw protein sources such as whey protein concentrate, the inventors have discovered that the centrifugation step should be avoided. In fact, it was discovered that the centrifugation step lowered the concentration of TGF-β1 or TGF-β2 in the samples by from about 5% to about 30%. While not wishing to be bound by this or any theory, it is believed that such losses may be attributable to delipidation and casein binding. As such, in preparing a nutritional product or raw protein source for ELISA testing for TGF-β1 or TGF-β2, the centrifugation step should be avoided altogether.

To activate latent TGF-β1 or TGF-β2 to the immunoreactive form which can be measured via the method of the invention, the TGF-β1 or TGF-β2 must be acid activated and neutralized. Although the activation procedure of acidifying and neutralizing is the same for all samples, the inventors have discovered that the ratio of sample:acid:base is different for samples of milk, nutritional products, and raw protein sources. In addition, the ratio of sample:acid:base also differs depending on whether TGF-β1 or TGF-β2 is being analyzed.

In an embodiment, activation of TGF-β1 or TGF-β2 in a sample of milk may be accomplished by adding an acid and a base in a ratio of sample:acid:base of about 1:0.2:0.2. In another embodiment, activation of TGF-β1 or TGF-β2 in a sample of nutritional composition may be accomplished by adding an acid and a base in a ratio of sample:acid:base of about 1:0.2:0.2.

In a separate embodiment, activation of TGF-β1 in a sample comprising a raw protein source may be accomplished by adding an acid and a base in a ratio of sample:acid:base of about 1:0.2:0.225. In another embodiment, activation of TGF-β2 in a sample comprising a raw protein source may be accomplished by adding an acid and a base in a ratio of sample:acid:base of about 1:0.2:0.2.

As an example of the activation procedure itself, not meant to be limiting, a 1 g sample of a nutritional composition or raw protein source may be weighed and placed in a 50 mL test tube. The sample may be reconstituted with 5 mL of water or phosphate buffered saline (PBS). The mixture may be stirred gently with a plastic rod. To this mixture, 1N HCl may be added in an amount to reach a pH of about 2 to about 3. The mixture may again be stirred with a plastic rod. The mixture may then be incubated at room temperature for 15 minutes. Next, 1N NaOH may be added to the mixture to obtain a pH of from about 7 to about 8. The mixture may again be mixed with a plastic rod. If the mixture has not already been reconstituted to its final concentration, it may be transferred to a 10 mL volumetric flask and brought to its final reconstitution concentration with water or PBS.

As another example, a liquid sample of milk, nutritional product, or raw protein source may be activated by transferring 1 mL of the liquid sample into a 2 mL lo-bind test tube. Concentrated HCl may be added to the sample to bring it to a pH of about 2 to about 3. The sample may be vortexed to mix and then incubated about room temperature for about 15 minutes. The sample may then be neutralized with 50% NaOH to reach a final pH of about 7 to about 8. The sample may again be vortexed to mix. Other acids or bases may be utilized in the activation step.

In an embodiment, polypropylene test tubes and flasks may be used in the invention because active TGF-β is highly hydrophobic and may stick to glass apparatus. The acid and base used in the method of the invention may be any known in the art. In an embodiment, the acid may be HCl and the base may be NaOH In the present invention, the sample is diluted using a buffer solution. Any buffer solution known in the art may be utilized in this embodiment. Two buffer solutions are provided by the Quantikine® kit (Cat. No. DB100B) for TGF-β1 quantification. The buffer solutions comprise RD1-21, a buffered protein solution with preservatives, and RD1-73, a buffered protein solution with preservatives. The inventors unexpectedly discovered that RD1-73, and not RD1-21, demonstrated linearity with a maximal slope for precise quantification of TGF-β1 and a wide concentration range to maximize the number of sample dilutions. This effect was noted for samples of milk, nutritional products, and raw protein sources. Thus, in an embodiment, the buffer solution used for dilution maybe RD1-73.

With regard to TGF-β2, if using the Quantikine® kit (Cat. No. DB250) for TGF-β2 quantification, assay diluent RD1-17 may be utilized.

Additionally, the inventors of the present invention have discovered that the ratio of initial dilution of the samples depends on whether TGF-β1 or TGF-β2 is being measured. Further, the initial dilution depends on whether the sample is milk, a nutritional product, or a raw protein source.

For example, in an embodiment, the initial dilution of samples of milk may be sample:diluent of from about 1:2 to about 1:5 for measurements of TGF-β1. In another embodiment, the initial dilution of samples of milk may be sample:diluent of from about 1:2 to about 1:3 for measurements of TGF-β1. In yet another embodiment, the initial dilution of samples of milk may be sample:diluent at least about 1:2 for measurements of TGF-β1. In a particular embodiment, the initial dilution of samples of milk may be sample:diluent of about 1:2 for measurements of TGF-1.

In an embodiment, no dilution is necessary for measurements of TGF-β2 in a milk source. In another embodiment, the initial dilution of samples of milk may be sample:diluent of at least about 1:2 for measurements of TGF-β2.

In another embodiment, the initial dilution of samples of a nutritional product may be sample:diluent of from about 1:3 to about 1:5 for measurements of TGF-β1. In yet another embodiment, the initial dilution of samples of a nutritional product may be sample:diluent of about 1:4 for measurements of TGF-β1. In still another embodiment, the initial dilution of samples of a nutritional product may be sample:diluent of at least about 1:4 for measurements of TGF-β1.

In another embodiment, the initial dilution of samples of a nutritional product may be sample:diluent of from about 1:5 to about 1:10 for measurements of TGF-β2. In another embodiment, the initial dilution of samples of a nutritional product may be sample:diluent of from about 1:7 to about 1:9 for measurements of TGF-β2. In yet another embodiment, the initial dilution of samples of a nutritional product may be sample:diluent of about 1:8 for measurements of TGF-β2. In still another embodiment, the initial dilution of samples of a nutritional product may be sample:diluent of at least about 1:8 for measurements of TGF-β2.

In another embodiment, the initial dilution of samples of a raw protein source may be sample:diluent of from about 1:1 to about 1:3 for measurements of TGF-β1. In yet another embodiment, the initial dilution of samples of a raw protein source may be sample:diluent of about 1:2 for measurements of TGF-β1. In still another embodiment, the initial dilution of samples of a raw protein source may be sample:diluent of at least about 1:2 for measurements of TGF-β1.

In another embodiment, the initial dilution of samples of a raw protein source may be sample:diluent of from about 1:5 to about 1:10 for measurements of TGF-β2. In another embodiment, the initial dilution of samples of a raw protein source may be sample:diluent of from about 1:8 to about 1:10 for measurements of TGF-β2. In yet another embodiment, the initial dilution of samples of a raw protein source may be sample:diluent of about 1:9 for measurements of TGF-β2. In still another embodiment, the initial dilution of samples of a raw protein source may be sample:diluent of at least about 1:9 for measurements of TGF-β2.

With the proper dilution ratio, the diluent may then be added to an assay well. The standard, control, or activated sample may then be added to each well. The microplate may then be tapped gently to mix, covered with an adhesive strip, and incubated for approximately two hours at room temperature.

Each well may be aspirated and washed, repeating the process three times for a total of four washes. The wells may be washed by filling each Well with a buffer using a squirt bottle, manifold dispenser, or autowasher. After the last wash, any remaining buffer may be removed by aspirating or decanting. The plate may then be inverted and blotted against clean paper towels.

In an embodiment, a TGF-β1 or TGF-β2 conjugate may then be added to each well containing a TGF-β1 or TGF-β2 sample, respectively. The wells may then be covered with a new adhesive strip and incubated for about two hours at room temperature. The aspiration/washing steps noted above may then be repeated.

A substrate solution (color reagent) may then be added to each well and incubated for about 30 minutes at room temperature in a dark place. An acid stop solution, such as $H_2SO_4$, may then be added to each well, tapping gently to ensure thorough mixing.

The optical density of each well may be determined within about 30 minutes using a microplate reader set to 450 nm. If wavelength correction is available, it may be set to 540 nm or 570 nm. If wavelength correction is not available, readings at 540 nm or 570 nm should be subtracted from the readings at 450 nm.

The user may then average duplicate readings for each standard, control, and sample and subtract the average zero standard optical density. A standard curve may be created by reducing the data using computer software capable of generating a four parameter logistic curve-fit. As an alternative, a standard curve may be constructed by plotting the mean absorbance for each standard on the y-axis against the concentration on the x-axis and drawing a best-fit curve through the points on the graph. The data may be linearized by plotting the log of the TGF-β1 concentrations versus the log of the O.D. and the best-fit line can be determined by regression analysis. If the samples Were diluted in the activation step, the measured concentrations should be multiplied by the final dilution factor.

The NIBSC/WHO reference parameters 89/518 (natural bovine) and 90/696 (recombinant human) have been evaluated using the method of the invention. The dose response of the TGF-β1 and TGF-β2 methods parallels the Quantikine® standard curve. The following equations have been determined for the conversion of sample values obtained with the Quantikine® TGF-β2 kit equivalent to NIBSC units.

$$NIBSC\ (89/518)\ \text{equivalent value (U/mL)} = 0.0551 \times \text{Quantikine® TGF-β2 value (pg/mL)}.$$

$$NIBSC\ (90/696)\ \text{equivalent value (U/mL)} = 0.0272 \times \text{Quantikine® TGF-β2 value (pg/mL)}.$$

The methods of the invention are beneficial in minimizing the matrix shift effect observed in infant formula during the analytical recovery testing. Accordingly, the present invention overcomes matrix shifts that contribute to an over- or under-estimation of the true TGF-β1 or TGF-β2 concentration in samples of milk, nutritional products, or raw protein sources.

The present invention further includes a kit for determining the bioactivity of TGF-β1 or TGF-β2 in human milk, nutritional products, or raw protein sources. The kit may include the RD1-73 buffer and/or the assay diluent RD1-17 and a porcine TGF-β standard. The kit may optionally further include one of more of a TGF-β conjugate, a TGF-β microplate, a calibrator diluent, a color reagent, and/or a wash buffer concentrate. Included with the kit are instructions to prepare the samples in accordance with the method described herein.

The following examples describe various embodiments of the present invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples. In the examples, all percentages are given on a weight basis unless otherwise indicated.

EXAMPLE 1

This example illustrates an embodiment of the present invention.

Equipments and Reagents
Tubes:
a. 50 mL polypropylene tubes
b. 10 ml volumetric flasks
c. 2 mL centrifuge tubes: (Protein LoBind 2.0 mL Tubes-Eppendorf 022431102)
Microplates and Accessories:
a. NUNC-Immuno MaxiSorp StarWell 96-Well Plates NUNC 441653
b. Sealing tape 96-well Pierce 15036
c. Reagent reservoir Pierce 15075
Microplate Reader and Accessories:
a. Microplate Washer Bio-Tek ELx405
b. Synergy™ HT Multi-Detection Microplate Reader Bio-Tek SIAFR
c. Gen5 Data Analysis Software Bio-Tek 594718
d. Microplate Shaker The Jitterbug Model 130000 (Boekel Scientific).
Pipettes: Single Channel:
a. 0.5-10 µL Eppendorf 022471902, Tips Eppendorf 2249152-1
b. 20-200 µL Eppendorf 022472054, Tips Eppendorf 2249154-7
c. 100-1000 µL Eppendorf 022472101, Tips Eppendorf 2249155-5
d. 0.5-5 mL Eppendorf 022472151, Tips Eppendorf 2249198-9
Multichannel:
a. 20-300 µL Eppendorf 022461460, Tips Eppendorf 2249154-7
b. 50-1200 µL Eppendorf 022461478, Tips Eppendorf 2249196-2
Buffers:
a. BupH Phosphate Buffered Saline (PBS) Pierce 28372
b. BupH carbonate-bicarbonate buffer Pierce 28382
c. Surfact Amp 20 Pierce 28320
Antigen Standards:
a. Recombinant human TGF-β2 standard (R&D Systems 302-B2)
Blocking Buffer: SEA Block Pierce 37527
Antibodies:
a. Anti-TGF-β2; Purified Mouse Monoclonal $IgG_{2B}$(R&D Systems MAB612)
b. Anti-TGF-β2; Biotinylated TGF-β2 Affinity Purified Goat IgG (R&D Systems BAF302)
ELISA Detection Kit:
a. Immunopure ultra-sensitive ABC peroxidase (Pierce 32050)
b. 1-step ultra-TMB-ELISA Reagent (Pierce 34028)
Stop Solution:
a. 1M H2SO4
Nanopure Water
Buffer Preparation:
CBC Buffer
a. One packet of Pierce BupH carbonate-bicarbonate buffer was dissolved in 500 mL water.
b. The solution was stored at room temperature.
c. The solution was stable for a few months.
PBS
a. One packet of Pierce BupH Phosphate Buffered Saline was dissolved in 500 mL water.
b. The solution was stored at room temperature.
c. The solution was stable for a few months.
PBST
a. One vial (10 ml) of Pierce Surfact Amp 20 was added to 2 L of PBS.
b. The solution was stored at room temperature.
c. The solution was stable for a few months.
Capture Antibodies: Anti-TGF-β2, Purified Mouse Monoclonal $IgG_{2B}$
a. 2 µg/mL antibody in PBS was prepared fresh for each assay.
Antigen Standard: Recombinant Human TGF-132 standard:
a. 0-4000 µg/mL in PBS was prepared fresh for each assay.
Detection antibody: Anti-TGF-β2; Biotinylated Affinity Purified Goat IgG:
a. 100 ng/ml antibody in PBS was prepared fresh for each assay.
Pierce ABC Reagent Solution:
a. For 10 mL PBS, 1 drop (45 µL) of reagent A Was added to 1 drop (45 µL) reagent B.
b. The solution was prepared fresh and stored at 4° C. until use.
Sample Preparation:

The following protocol was utilized for TGF-β2 activation in a powdered sample of a nutritional product.

1. A 1 g sample was weighed and placed in a 50 ml tube.
2. The sample was reconstituted with 5 ml of PBS.
3. The sample was mixed gently with a plastic rod.
4. 1N HCl was added to the sample to reach a pH of 2 to 3. The sample was then mixed with a plastic rod.
5. The sample was incubated at room temperature for 15 min.
6. 1N NaOH was added to the sample to reach a pH of 7 to 8. The sample was then mixed with a plastic rod.
7. The sample was transferred to a 10 ml volumetric flask and brought to final volume with PBS (Final concentration: 100 mg/ml).

The following protocol was utilized for TGF-β2 activation in liquid sample of milk.

1. 1 ml of liquid sample was transferred into a 2 ml lo-bind tube.

2. Concentrated HCl was added to reach a pH of 2 to 3. The mixture was vortexed to mix.

3. The mixture was incubated at room temperature for 15 min.

4. 50%/50% concentrated NaOH/$H_2O$ was added to reach a pH of 7 to 8. The sample was vortexed to mix.

TABLE 1

Serial dilutions for standard

| rhTGF-β2 standard stock concentration (pg/ml) | Volume of stock/ previous dilution (ul) | Buffer (PBS) (ul) | Final concentration (pg/ml) |
|---|---|---|---|
| 2,000,000 | 4 (stock) | 1996 | 4000 |
|  | 1000 | 1000 | 2000 |
|  | 1000 | 1000 | 1000 |
|  | 1000 | 1000 | 500 |
|  | 1000 | 1000 | 250 |
|  | 1000 | 1000 | 125 |
|  | 1000 | 1000 | 62.5 |
|  | 1000 | 1000 | 31.25 |
|  | 0 | 2000 | 0 |

TABLE 2

Serial dilutions for samples

| Sample initial concentration (mg/ml) | Volume of initial/ previous dilution (ul) | Buffer (PBS) (ul) | Final concentration (ug/ml) |
|---|---|---|---|
| 100 | 1000 (stock) | 0 | 100,000 |
|  | 500 | 500 | 50,000 |
|  | 500 | 500 | 25,000 |
|  | 500 | 500 | 12,500 |
|  | 500 | 500 | 6,250 |
|  | 500 | 500 | 3,125 |

Procedure 1. 100 μL of capture antibody solution was pipetted to each well and covered with sealing tape.

2. The sample was incubated overnight at 4° C.

3. The plate was washed three times with PBST.

4. 270 μL Blocking buffer was pipetted into the plate and the plate was covered with sealing tape.

5. The plate was incubated for 1 hour at room temperature (RT).

6. The plate was then washed three times with PBST.

7. 100 μL standard was pipetted into the samples, which were then covered with sealing tape.

8. The mixture was then incubated for 1 hour and 30 minutes at RT with shaking.

9. The plate was then washed three times with PBST.

10. 100 μL of detection antibody was pipetted into the plate and the plate was covered with sealing tape.

11. The sample was incubated for 2 hours at RT with shaking.

12. The plate was then washed three times with PBST.

13. 100 μL ABC reagent was then pipetted into the sample and the sample was covered with sealing tape.

14. The sample was incubated for 1 hour at RT with shaking.

15. The plate was then washed three times with PBST.

16. 100 μL chromogen (Pierce Ultra-TMB) substrate was pipetted into the sample and incubated for a few minutes at RT. The color developed within 5 minutes.

17. 100 μL of 1M $H_2SO_4$ was added to the sample to stop the reaction and the sample was measured ($A_{450}/A_{652}$ nm) using a microplate reader.

TABLE 3

Standard Curve

| Curve Name | Curve Formula | A | B | R | $R^2$ |
|---|---|---|---|---|---|
| Curve | Y = A * X + B | 0.000349 | −0.0137 | 0.999 | 0.998 |

TABLE 3

96-Well Plate Layout:

| STD 1 | STD 2 | STD 3 | STD 4 | STD 5 | STD 6 | STD 7 | STD 8 | STD 9 | CTL | CTL | Blank |
|---|---|---|---|---|---|---|---|---|---|---|---|
| STD 1 | STD 2 | STD 3 | STD 4 | STD 5 | STD 6 | STD 7 | STD 8 | STD 9 | CTL | CTL | Blank |
| Sample 1; dilution 6 | Sample 1; dilution 5 | Sample 1; dilution 4 | Sample 1; dilution 3 | Sample 1; dilution 2 | Sample 1; dilution 1 | Sample 3; dilution 1 | Sample 3; dilution 2 | Sample 3; dilution 3 | Sample 3; dilution 4 | Sample 3; dilution 5 | Sample 3; dilution 6 |
| Sample 1; dilution 6 | Sample 1; dilution 5 | Sample 1; dilution 4 | Sample 1; dilution 3 | Sample 1; dilution 2 | Sample 1; dilution 1 | Sample 3; dilution 1 | Sample 3; dilution 2 | Sample 3; dilution 3 | Sample 3; dilution 4 | Sample 3; dilution 5 | Sample 3; dilution 6 |
| Sample 1; dilution 6 | Sample 1; dilution 5 | Sample 1; dilution 4 | Sample 1; dilution 3 | Sample 1; dilution 2 | Sample 1; dilution 1 | Sample 3; dilution 1 | Sample 3; dilution 2 | Sample 3; dilution 3 | Sample 3; dilution 4 | Sample 3; dilution 5 | Sample 3; dilution 6 |
| Sample 2; dilution 6 | Sample 2; dilution 5 | Sample 2; dilution 4 | Sample 2; dilution 3 | Sample 2; dilution 2 | Sample 2; dilution 1 | Sample 4; dilution 1 | Sample 4; dilution 2 | Sample 4; dilution 3 | Sample 4; dilution 4 | Sample 4; dilution 5 | Sample 4; dilution 6 |
| Sample 2; dilution 6 | Sample 2; dilution 5 | Sample 2; dilution 4 | Sample 2; dilution 3 | Sample 2; dilution 2 | Sample 2; dilution 1 | Sample 4; dilution 1 | Sample 4; dilution 2 | Sample 4; dilution 3 | Sample 4; dilution 4 | Sample 4; dilution 5 | Sample 4; dilution 6 |
| Sample 2; dilution 6 | Sample 2; dilution 5 | Sample 2; dilution 4 | Sample 2; dilution 3 | Sample 2; dilution 2 | Sample 2; dilution 1 | Sample 4; dilution 1 | Sample 4; dilution 2 | Sample 4; dilution 3 | Sample 4; dilution 4 | Sample 4; dilution 5 | Sample 4; dilution 6 |

FIG. 1 illustrates the standard curve.

TABLE 4

Results

| Well ID | Name | Well | Conc/Dil | Blank 450 | Conc | Count | Mean | Std Dev | CV (%) |
|---|---|---|---|---|---|---|---|---|---|
| Sample 1 | | C6 | 1.00E+05 | 0.907 | 2633.964 | 3 | 2572.918 | 372.903 | 14.493 |
| | | D6 | 1.00E+05 | 1.004 | 2911.532 | | | | |
| | | E6 | 1.00E+05 | 0.746 | 2173.259 | | | | |
| | | C5 | 50000 | 0.655 | 1912.861 | 3 | 1853.723 | 70.636 | 3.81 |
| | | D5 | 50000 | 0.607 | 1775.508 | | | | |
| | | E5 | 50000 | 0.641 | 1872.8 | | | | |
| | | C4 | 25000 | 0.379 | 1123.082 | 3 | 1085.882 | 42.153 | 3.882 |
| | | D4 | 25000 | 0.369 | 1094.467 | | | | |
| | | E4 | 25000 | 0.35 | 1040.098 | | | | |
| | | C3 | 12500 | 0.17 | 525.024 | 3 | 527.886 | 13.113 | 2.484 |
| | | D3 | 12500 | 0.176 | 542.193 | | | | |
| | | E3 | 12500 | 0.167 | 516.44 | | | | |
| | | C2 | 6250 | 0.079 | 264.626 | 3 | 256.995 | 6.608 | 2.571 |
| | | D2 | 6250 | 0.075 | 253.18 | | | | |
| | | E2 | 6250 | 0.075 | 253.18 | | | | |
| | | C1 | 3125 | 0.039 | 150.165 | 3 | 121.55 | 24.946 | 20.523 |
| | | D1 | 3125 | 0.023 | 104.381 | | | | |
| | | E1 | 3125 | 0.025 | 110.104 | | | | |
| Sample 2 | | F6 | 1.00E+05 | 0.605 | 1769.785 | 3 | 1807.939 | 116.388 | 6.438 |
| | | G6 | 1.00E+05 | 0.586 | 1715.416 | | | | |
| | | H6 | 1.00E+05 | 0.664 | 1938.615 | | | | |
| | | F5 | 50000 | 0.384 | 1137.389 | 3 | 1165.051 | 52.945 | 4.544 |
| | | G5 | 50000 | 0.382 | 1131.666 | | | | |
| | | H5 | 50000 | 0.415 | 1226.096 | | | | |
| | | F4 | 25000 | 0.203 | 619.454 | 3 | 668.1 | 50.138 | 7.505 |
| | | G4 | 25000 | 0.238 | 719.607 | | | | |
| | | H4 | 25000 | 0.219 | 665.239 | | | | |
| | | F3 | 12500 | 0.094 | 307.549 | 3 | 339.025 | 28.183 | 8.313 |
| | | G3 | 12500 | 0.113 | 361.918 | | | | |
| | | H3 | 12500 | 0.108 | 347.61 | | | | |
| | | F2 | 6250 | 0.046 | 170.196 | 3 | 184.503 | 17.87 | 9.686 |
| | | G2 | 6250 | 0.049 | 178.78 | | | | |
| | | H2 | 6250 | 0.058 | 204.534 | | | | |
| | | F1 | 3125 | 0.023 | 104.381 | 3 | 92.935 | 15.142 | 16.293 |
| | | G1 | 3125 | 0.013 | 75.766 | | | | |
| | | H1 | 3125 | 0.021 | 98.658 | | | | |

Calculation $$\text{Antigen Concentration (ppm)} = \frac{\text{(Measured conc. in pg/ml)}}{\text{(Sample dilution in ug/ml)}} \quad \text{Eq. 1}$$

TABLE 5

Concentrations

| Sample | Concentration (ug/ml) | TGF-B2 (pg/ml) | CV (%) | TGFB2 (pg/ug) ppm | % Change From Previous conc. | Average TGF-B2 (pg/ug) ppm |
|---|---|---|---|---|---|---|
| Sample 1 | 1.00E+05 | 2572.918 | 14.493 | 0.0257 | | |
| | 50000 | 1853.723 | 3.81 | 0.0371 | 144.09 | |
| | 25000 | 1085.882 | 3.882 | 0.0434 | 117.16 | |
| | 12500 | 527.886 | 2.484 | 0.0422 | 97.23 | 0.0409 |
| | 6250 | 256.995 | 2.571 | 0.0411 | 97.37 | |
| | 3125 | 121.55 | 20.523 | 0.0389 | 94.59 | |
| Sample 2 | 1.00E+05 | 1807.939 | 6.438 | 0.0181 | | |
| | 50000 | 1165.051 | 4.544 | 0.0233 | 128.88 | |
| | 25000 | 668.1 | 7.505 | 0.0267 | 114.69 | 0.0227 |
| | 12500 | 339.025 | 8.313 | 0.0271 | 101.49 | |
| | 6250 | 184.503 | 9.686 | 0.0295 | 108.84 | |
| | 3125 | 92.935 | 16.293 | 0.0297 | 100.74 | |

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged both in whole or in part. For example, while methods for the production of a commercially sterile liquid nutritional supplement made according to those methods have been exemplified, other uses are contemplated. Therefore, the spirit and scope of the appended claims should not be limited to the description of the preferred versions contained therein.

What is claimed is:

1. A method for determining the level of TGF-β1 in a sample of powdered nutritional product, the method comprising:

a. reconstituting the sample to a concentration of from about 160 mg/mL to about 170 mg/mL;
b. avoiding a centrifuging step;
c. activating the sample by adding an acid and a base in a ratio of sample:acid:base of about 1:0.2:0.2;
d. diluting the sample using a buffer solution;
e. determining the concentration of TGF-$\beta$1 in the sample comprising the steps:
  i. adding an antibody specific for TGF-$\beta$1 to at least one well of a microplate;
  ii. adding the diluted sample of step(d) to the at least one well of the microplate;
  iii. adding at least one detection antibody to the at least one well of the microplate to form a complex with any TGF-$\beta$1 in the sample;
  iv. adding at least one enzymatic substrate to the at least one well of the microplate to produce a visible signal;
  v. adding a detection reagent to the at least one well of the microplate;
  vi. detecting the visible signal with a microplate reader to determine the amount of TGF-$\beta$1 in the sample.

2. The method of claim 1 wherein the sample is reconstituted to a concentration of about 166 mg/mL.

3. The method of claim 1 wherein the reconstitution step comprises adding 3.0 mL water to 0.5 g sample.

4. The method of claim 1 wherein the ratio of sample:buffer in the dilution step is about 1:4.

5. The method of claim 1 wherein the sample is selected from the group consisting of a nutritional supplement, children's nutritional product, infant formula, and human milk fortifier.

* * * * *